United States Patent [19]
Cohen et al.

[11] 3,985,711
[45] Oct. 12, 1976

[54] DICARBOXYLIC COMPOUNDS HAVING 2,4-QUINAZOLINEDIONE RINGS AND POLYESTER RESINS DERIVED THEREFROM

[75] Inventors: Choua Cohen, Grenoble; Bruno Durif-Varambon, Eybens; Robert Salle; Bernard Sillion, both of Grenoble, all of France

[73] Assignee: Institut Francais du Petrole, des Carburants et Lubrifiants et Entreprise de Recherches et d'Activities Petrolieres Elf, Rueil-Malmaison, France

[22] Filed: Mar. 5, 1975

[21] Appl. No.: 555,431

Related U.S. Application Data

[62] Division of Ser. No. 288,478, Sept. 13, 1972, Pat. No. 3,882,121.

[30] Foreign Application Priority Data

Sept. 15, 1971 France .............................. 71.33327
Apr. 10, 1972 France .............................. 72.12565

[52] U.S. Cl.............................. 260/75 N; 260/75 S
[51] Int. Cl.² ......................................... C08G 63/18
[58] Field of Search............ 260/75 N, 256.4 Q, 260

[56] References Cited
UNITED STATES PATENTS 3,728,348  4/1973  Lee ................... 260/75 N
3,781,288  12/1973  Rosenfeld ........... 260/260

FOREIGN PATENTS OR APPLICATIONS 1,478,938  3/1967  France

Primary Examiner—Paul R. Michl
Attorney, Agent, or Firm—Millen, Raptes & White

[57] ABSTRACT

A dicarboxylic compound complying with one of the general formulae:

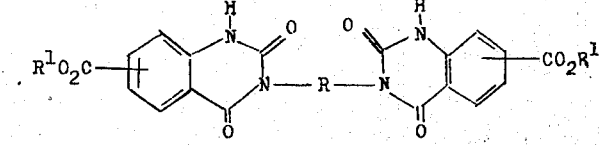

in which R is a divalent radical selected from the aliphatic, alicyclic and aromatic radicals, the aliphatic containing 1–20 carbon atoms and the other containing from 5 to 20 carbon atoms, $R^1$ is selected from the hydrogen atom and the alkyl and cycloalkyl groups containing from 1 to 10 carbon atoms and $R^2$ is selected from the alkyl and cycloalkyl groups containing from 1 to 10 carbon atoms, the polyester resins derived therefrom being usable as enamelling composition, particularly for coating metal wires.

19 Claims, No Drawings

DICARBOXYLIC COMPOUNDS HAVING 2,4-QUINAZOLINEDIONE RINGS AND POLYESTER RESINS DERIVED THEREFROM

This is a division of application Ser. No. 288,478 filed Sept. 13, 1972 now U.S. Pat. No. 3,882,121 issued May 6, 1975.

This invention relates to dicarboxylic compounds having 2,4-quinazolinedione rings and their process of manufacture.

It also relates to the use of these dicarboxylic compounds having 2,4-quinazolinedione rings in the manufacture of new resins and particularly of polyester resins.

It also concerns new polyester resins having 2,4-quinazolinedione rings. It has also for object the use of these new polyester resins in the manufacture of coating materials and particularly varnishes for enamelling metallic electric conductors.

For the manufacture of enamelling varnishes, particularly for the metallic electric conductors, it has already been proposed, according to the French Pat. Nos. 1,368,741, 1,478,938, 1,511,961, and in the French patent application Ser. No. 2,009,052, to make use of polyester-imide resins which consist generally either of condensation products prepared from reactants already containing cyclic imide groups, or of condensation products in which the formation of imide cycles occurs during the condensation of the reactants.

The invention has for object to provide new polymeric substances free of imide cycles, which make it possible to prepare, at low cost, coating compositions exhibiting a remarkable thermal stability and high softness and adhesive properties, these properties being such that they can be used advantageously for manufacturing insulating varnishes suitable for enamelling metal electric conductors.

The invention has also for object to provide insulating varnishes for metal electric conductors which exhibit the required electrical, thermal, mechanical and chemical properties and particularly a resistance to heat which make possible their use over a long period at high temperatures, particularly a continuous operation at temperature of 180°C or more (H class of insulating materials).

It has as a further object to provide new compounds which may be prepared at low cost and which can be used advantageously as starting materials in the manufacture of the above-mentioned polymeric substances.

The invention has, as more particular object, to provide new dicarboxylic compounds, containing in their molecule one or more 2,4-quinazolinedione rings.

According to this invention these new compounds are dicarboxylic acids or mono- or di-esters of dicarboxylic acids complying with one of the following general formulae:

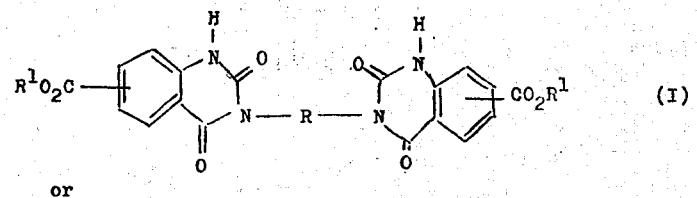

or

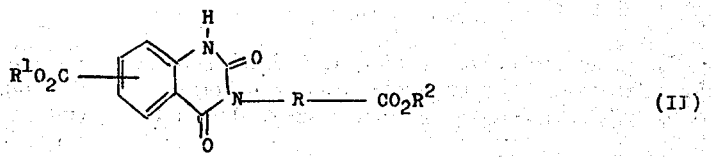

in which R is a divalent radical selected from the aliphatic, alicyclic and aromatic radicals the aliphatic containing 1–20 carbon atoms and the other containing from 5 to 20 carbon atoms; $R^1$ is selected from the hydrogen atom and alkyl and cycloalkyl groups containing from 1 to 10 carbon atoms, and $R^2$ is selected from alkyl and cycloalkyl groups containing from 1 to 10 carbon atoms.

These dicarboxylic compounds may be prepared from amino-dicarboxylic acids or from mono or diesters of such acids, complying with the general formula:

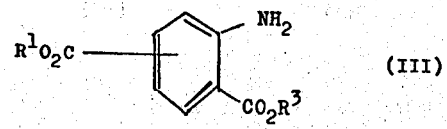

in which $R^1$ is defined as above and $R^3$ is selected from the hydrogen atom and alkyl and cycloalkyl groups containing from 1 to 10 carbon atoms; $R^1$ and $R^3$ being the same or different, one of the carboxylic groups being obligatorily in ortho position with respect to the amino group, the other carboxylic group having any position.

The dicarboxylic acids, the mono and diesters complying with the general formula (I) may be obtained by reacting one compound of the formula (III) with a diisocyanate of the general formula:

in which R is defined as above, or with an alkyl or aryl diurethane of such a diisocyanate (so-called "hidden" diisocyanate).

There is generally used a molar ratio of the aminodicarboxylic compound (III) to the diisocyanate (IV) of at least 2. There is obtained an intermediary bis-urea (V) which may be converted immediately or in a further stage into bis (2,4-quinazolinedione) by cyclisation accompanied with the removal of water or alcohol.

The reaction conforms with the following scheme:

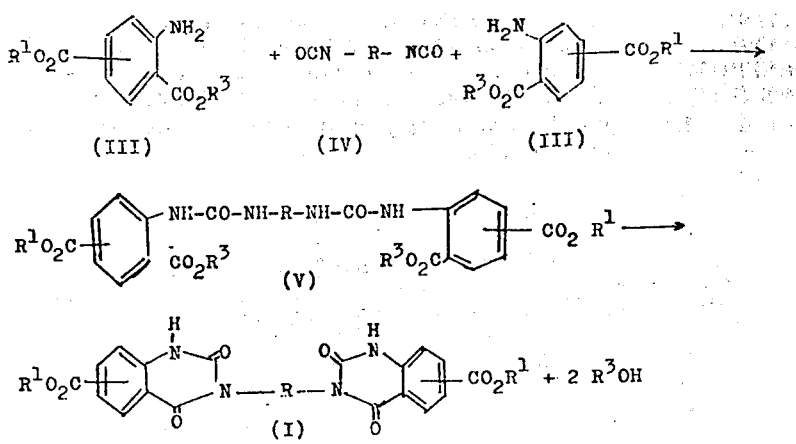

The mono and diesters complying with the general formula (II) may be prepared by reacting a compound of formula (III) with an isocyanate of general formula:

in which R and $R^2$ have the same meaning as above, or with an alkyl or aryl urethane of such an isocyanate (so-called hidden isocyanate).

The manufacturing procedure which comprises adding the isocyanate to an amine group of the aminodicarboxylic compound with the formation of intermediary urea (VII) followed with the cyclisation of the urea to 2,4-quinazolinedione, is as follows:

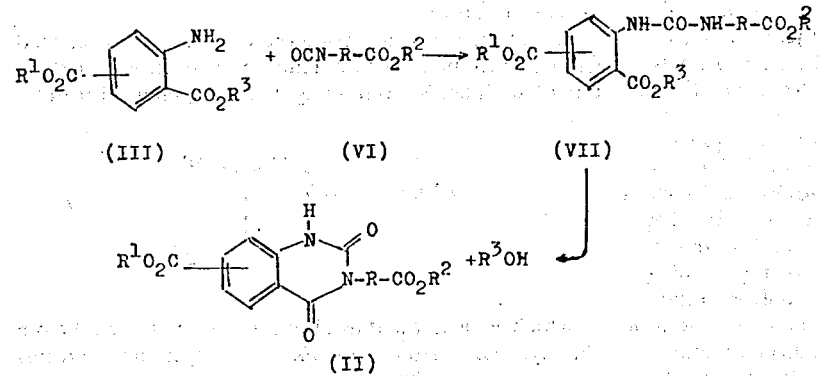

As examples of diisocyanates conforming with the formula (VI) above, there can be mentioned:

Polymethylene-diisocyanates of general formula

in which n for example is a number from 4 to 8, the phenylene-diisocyanates (optionally substituted with alkyl groups or halogen atoms) such as for example the m-and p-phenylene diisocyanates, the 2,4 and 2,6 tolylene-diisocyanates, the ethylbenzene-diisocyanates or the chloro p-phenylene diisocyanate; the 4,4'-diisocyanato-diphenylmethane; the 4,4'-diisocyanato-diphenylether, the 4,4'-diisocyanato-biphenyle or the diisocyanato-naphthalenes.

The isocyanates of the general formula (VI), the use of which is preferred according to this invention, are the aliphatic or aromatic isocyanates, which further contain an alkyl or cycloalkyl ester function.

As examples there can be mentioned: the esters of isocyanato-acetic acid (R contains 1 carbon atom) the esters of α or β -isocyanato-propionic acid (R contains 1 carbon atom), the esters of isocyanato-butyric acid (R contain 1 carbon atom), the esters of isocyanato-undecanoic acid, the esters of 3- or 4-isocyanato-benzoic acid, or the esters of the isocyanato-naphthoic acid.

As examples of aminodicarboxylic compounds, complying with general formula (III), there can be mentioned:

The 2-amino terephthalic, 2-amino-5 -bromo terephthalic, 3-amino phthalic, 2-amino isophthalic; 2-amino 5-methyl isophthalic acids and the alkyl and cycloalkyl esters of said acids.

The reaction between the isocyanate compound of formula (IV) or (VI) and the amino-dicarboxylic compound of formula (III) may be conducted according to various methods.

When the aminodicarboxylic compound (III) is a dicarboxylic acid or a mono-ester, i.e. when at least one of the radicals $R^1$ and $R^3$ is the hydrogen atom, it is possible to proceed to an interfacial reaction, for example, by dissolving said amino-dicarboxylic compound in an alkaline aqueous solution and adding to the solution, under stirring, the isocyanate compound dissolved in an organic solvent immiscible with water. The reaction may also be conducted in solution in a solvent inert with respect to the isocyanates such, for example, as the hydrocarbon solvents, pyridine, dioxane, dimethylacetamide, dimethylformamide, or N-methylpyrrolidone, provided that the solvents of the amide type be used only when the reaction temperature is very substantially lower than their reaction temperature with the isocyanates.

The reactions in solution are preferably conducted at temperatures lower than 100°C in order to prevent secondary reactions of addition of one or more isocyanate groups onto a free carboxylic group.

It is possible, if so desired, to increase the reaction velocity by adding an usual catalyst such, for example, as a metal alcoholate or a tertiary amine.

When the reaction is conducted at low temperature (for example lower than 60°C), there is essentially obtained an intermediate urea complying with formula (V) or (VII). The stage for obtaining the final compound (I) or (II), i.e. the cyclisation reaction of the urea to the 2,4-quinazolinedione heterocycle, may be achieved in various manners, for example, in a thermal or chemical way. The thermal treatment may be carried out either in the absence of solvent, or in a high boiling solvent, optionally in the presence of a catalyst (preferably pyridine), generally at a temperature from 100° to 300°C. The chemical cyclisation consists of treating the intermediary urea (V) or (VII) by a dehydrating agent such, for example, as sulfuric acid, polyphosphoric acid or an anhydride of a carboxylic acid such as acetic anhydride, in the presence or the absence of a catalyst.

When a diester is used as amino-dicarboxylic compound (III), i.e. when $R^1$ and $R^3$ are each an alkyl or cycloalkyl group, the reaction may be conducted with the isocyanate compound by heating in the presence or the absence of a solvent. The reaction temperature is generally from 50° to 220°C, and preferably at least 100°C. It is obvious that the use of a hidden isocyanate requires a sufficiently high reaction temperature in order that the isocyanate itself be released.

The reaction time depends on the operating conditions and of the reactants, but in most cases, it is from 5 to 48 hours.

The solvents to be used in this reaction must be inert with respect to the reactants, or must react with them in a reversible manner, this being, for example, the case of the alcohols or phenols with respect to the isocyanates; other examples of solvents which can be used are: hydrocarbons, aliphatic or alicyclic ethers, pyridine, dimethylforamide, dimethylacetamide or N-methyl-pyrrolidone, provided that the solvents of the amide type are always used when the reaction temperature is substantially lower than their reaction temperature with the isocyanates.

It is possible, if so desired, to increase the velocity of the reaction of addition onto the isocyanates by making use of a conventional catalyst, such for example, as a tertiary amine.

Generally the reaction is carried out, with substantially stoichiometrical amounts of the reactants, but the reaction may also be conducted in the presence of a slight excess of the amino-carboxylic compound.

When the reaction is conducted at a sufficiently high temperature (generally higher than 100°C), there are obtained quinazolinediones diesters (I) or (II) directly, the cyclisation reaction of the intermediate urea being effected during the heating step.

The structure of the products obtained according to the above-mentioned methods may be determined by elementary analysis or from the infrared absorption spectrum, which shows, in particular, characteristic absorption bands in the vicinity of 1720 and 1670 cm$^{-1}$ (as mentioned for example by A. R. KATRIZKY in Physical Methods in Heterocyclic chemistry, Academic press, (1963), vol. II, page 270).

The dicarboxylic compounds having 2,4-quinazolinedione rings such as above-described, may be used as starting materials in the manufacture of various polymeric substances and particularly of polyesters and polyamides.

For the manufacture of polyester resins which are the main object of this invention, the most suitable dicarboxylic compounds are those complying with general formulae (I) and (II) in which radicals R are aromatic radicals, radicals $R^1$ are selected from the hydrogen atom and the alkyl radicals having from 1 to 6 carbon atoms and radical $R^2$ is an alkyl radical having from 1 to 6 carbon atoms.

The polyester 2,4-quinazolinedione resins, according to the invention, are hereunder defined as being formed of a "polycarboxylic component" and of a "polyhydroxyl component".

By these terms, there are meant the totality of the multivalent groups of the type A [—CO—]$_m$ contained in the polyester, where the CO groups are ester carbonyles, A is the radical of the corresponding polycarboxylic acid, and the integer $m$ indicates its "functionality" (which may be for example, 2, 3 or 4), and the totality of the multivalent groups of the type B [—O—]$_n$ contained in the polyester, in which the divalent oxygen atoms derive from hydroxyl groups, B is the radical of the corresponding polyol and the integer $n$ indicates its "functionality" (which may be for example 2, 3, 4 or more).

The polyester-2,4-quinazolinedione resin according to the invention, is characterized in that its polycarboxylic component is derived, in a proportion of 10 to 100% (preferably from 20 to 50%) of the carboxylic acid equivalents, from at least one dicarboxylic acid containing one or two 2,4-quinazolinedione groups, and complying with one of the following formulae:

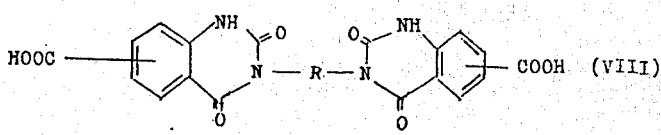

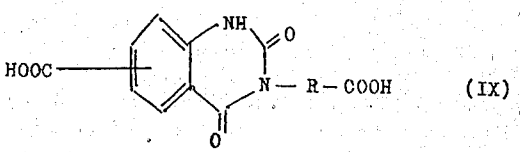

in which the radical R is defined as above; in a proportion of 0 to 90% (preferably from 50 to 80%) of the carboxylic acid equivalents, from at least one polycarboxylic aromatic acid (for example di-, tri- or tetracarboxylic); and in a proportion of 0 to 10% of the carboxylic acid equivalents, from at least one aliphatic dicarboxylic acid, which contains, for example, from 4 to 10 carbon atoms; and in that its polyhydroxyl component is derivated in a proportion of 50 to 100% of the hydroxyl equivalents, from at least one polyol containing at least three hydroxyl groups and, in a proportion of 0 to 50% of the hydroxyl equivalents, from at least one aliphatic or cycloaliphatic diol which contains, for example, from 2 to 10 carbon atoms.

The preferred dicarboxylic acids of formulae (VIII) and (IX) are those in which R is an aromatic radical, which may contain a single aromatic cycle, several joined aromatic cycles, or still several aromatic rings, separate or condensed, interconnected through a single bond, a divalent atom or a divalent group such as, for example, —O—, —S—, —SO—, —SO$_2$—, or —CH$_2$—.

As examples of such dicarboxylic acids, there can be mentioned, as more particularly preferred, those in which R is a phenylene radical (for example 1,3-phenylene or 1,4-phenylene), tolylene, or a divalent radical derivated from diphenylmethane or diphenylether.

As examples of polycarboxylic aromatic compounds, there are to be mentioned: isophthalic acid, terephthalic acid, 4,4'-diphenyl-ether dicarboxylic acid, trimesic acid and trimellitic acid, the preferred acid being terephthalic acid.

The aliphatic dicarboxylic acids include for example: maleic, adipic, azelaic and sebacic acids.

The polyols containing at least three hydroxyl groups include for example aliphatic triols such as glycerol, 1,1,1-trimethylol ethane or 1,1,1-trimethylol propane, aliphatic tetrols such as pentaerythritol, aliphatic hexols, such as sorbitol or mannitol, or still heterocyclic triols such as tris (hydroxyethyl) isocyanurate, or tris (hydroxypropyl) isocyanurate, the preferred polyol being the tris (hydroxyethyl) isocyanurate which hereinafter will be shortnamed, T.H.E.I.C.

As examples of aliphatic or cycloaliphatic diols, there may be mentioned: ethyleneglycol, 1,4-butanediol, 1,5-pentanediol, neopentylglycol, 1,6-hexanediol, 1,6-trimethylhexanediol or 1,4-cyclohexanediol, the preferred diols being ethyleneglycol and neopentylglycol.

The polyester-2,4-quinazolinedione resins according to this invention may be prepared according to any known direct esterification or transesterification technique, from convenient amounts of the polycarboxylic reactants and of the suitable polyhydroxylated reactants.

As a general rule, a plurality of polycarboxylic compounds including:

in a proportion of 10 to 100%, (preferably from 20 to 50%) of the carboxylic functions involved, at least one of the dicarboxylic compounds having 2,4-quinazolinedione rings which comply with formulae (I) and (II) hereabove mentioned, in a proportion of 0 to 90% (preferably from 50 to 80%) of the carboxylic functions involved, at least one of the above-defined polycarboxylic aromatic acids and one or or more of their lower alkyl esters, and in a proportion of 0 to 10% of the carboxylic functions involved, at least one of the above-defined aliphatic dicarboxylic acids and/or at least one of their lower alkyl esters, are caused to react with a plurality of polyhydroxylated compounds comprising:

in a proportion of 50 to 100% of the hydroxyl functions involved, at least one polyol containing at least three hydroxyl functions, selected for example, among the abovementioned ones, and in a proportion of 0 to 50% of the hydroxyl functions involved, at least one aliphatic or cycloaliphatic diol, selected for example among those mentioned above.

In the foregoing, by "lower alkyl" there is meant an alkyl radical having from 1 to 6 carbon atoms. In most cases the methyl ester is used.

Among the dicarboxylic compounds having 2,4-quinazolinedione cycles, which can be used for the manufacture of the polyester resins according to the invention, specific compounds are especially interesting, and this is particularly the case of the following methyl esters:

2,4-bis-tolylene [(7-methoxycarbonyl 2,4-quinazolinedione)-3-yl] of the formula:

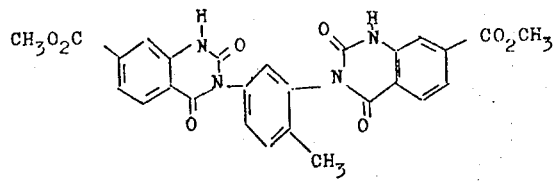

4,4' methylene biphenylene-bis[(7-methoxycarbonyl 2,4-quinazolinedione)3-yl] of the formula;

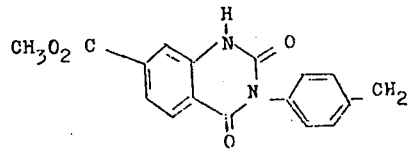

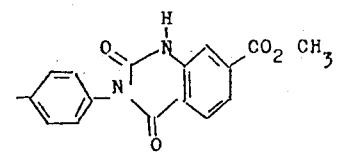

4,4'-oxy biphenylene-bis[(7-methoxycarbonyl 2,4-quinazolinedione)3-yl] of the formula:

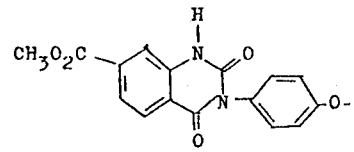

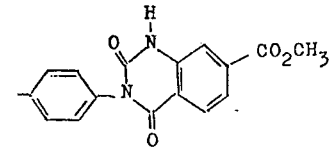

or still 3-(p.methoxycarbonylphenyl) 7-methoxycarbonyl 2,4-quinazolinedione, of the formula

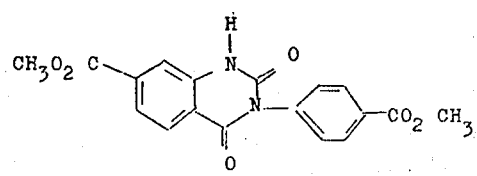

It is essential, in order to obtain resins exhibiting satisfactory properties, that the polycarboxylic reactants and the polyhydroxylated reactants be introduced in such proportions that the ratio of the sum of the hydroxyl functions to the sum of the carboxylic functions be higher than 1 and preferably from 1.1 to 2.

The direct esterification or the transesterification reaction may be advantageously conducted in a signal step at a temperature of 150° to 230°C (preferably from 190° to 220°C) and in the presence of an esterification or transesterification catalyst, consisting preferably of a tetra alkyl titanate whose alkyl groups contain from 1 to 6 carbon atoms.

It is preferred to proceed in solution in a solvent whose boiling point is higher than 190°C, such as N-methylpyrrolidone, cresylic acid, m-cresol or a mixture of cresols; the amount of solvent used is generally low, a porportion of dry substances of 60 to 90% by weight being generally convenient. The reaction time depends on the nature of the reactants, their proportions, the selected catalyst and solvent, as well as the temperature; for example, when the reaction is conducted at a temperature from 190° to 220°C, the heating is performed over a period of generally from 6 to 20 hours. It is preferable, during the reaction time, to release the volatile compounds formed in the esterification or transesterification reaction (water or alcohols). They may be recovered, and from their measured amount it is possible to estimate the degree of advance of the reaction.

In the manufacture of polyester -2,4-quinazolinedione resins according to the invention, the dicarboxylic compounds with 2,4-quinazolinedione rings may be used as pure compounds, but it is also possible, in order to avoid their separation from the reaction medium where they have been synthetized, to proceed by directly adding to the raw product resulting from their synthesis, the other reactants required for the manufacture of the polyester-2,4-quinazolinedione resins and to subject the resulting mixture to the above-mentioned reaction conditions.

The polyester-2,4-quinazolinedione resins, according to the invention, may be used particularly for the manufacture of coatings, more specially varnishes for enamelling metal electric conductors.

According to the method used for their manufacture, the polyester quinazolinedione resins according to the invention may be obtained in the form of solutions in a solvent or in a mixture of solvents, such as those above-mentioned.

These solutions may be used as base varnishes for the manufacture of coating compositions, and particularly of enamelling varnishes for metal electric conductors. These base varnishes may be diluted by addition of one of the above-mentioned solvents or of a mixture of several of such solvents. They can also be diluted with aliphatic or aromatic hydrocarbons or still with aromatic hydrocarbon cuts, having preferably a boiling point higher than 100°C.

In order to improve the capability of use of these base varnishes, particularly as coatings for metal electric conductors, it is possible to add thereto various ingredients, which generally are allowed to react therewith, either at cold, or by heating carried out for example during a period of from 1 to 4 hours, at a temperature of 90° to 180°C.

Thus, there can be added thereto an alkyl titanate, such as hereabove defined, for example in a proportion of 0.1 to 10% by weight of the dry substance of the varnish.

There can be also added thereto, for example in a proportion of 1 to 15% by weight, a polyisocyanate such as for example, a so-called "blocked" triisocyanate produced by trimerizing 2,4-diisocyanate tolylene and blocked for example by means of phenol (such as the products known under the trade marks "Mondur S", "Desmodur CTS" and "Mondur SH").

There can be also added, for example in a proportion of 0.1 to 1by weight, a metallic drying agent, such as for example, a metal octoate or naphthenate.

It may be also advantageous to incorporate to the varnish, for example in a proportion of 1 to 15% by weight, a phenolaldehyde resin, such for example as a phenol-formaldehyde, cresol-formaldehyde, or still melamine-formaldehyde resin.

An addition of biphenyle, for example in a proportion of 0.5 to 2.5% by weight, may, in some cases, improve the surface state of the coatings obtained by means of the varnishes.

The above-indicated proportions are expressed as a weight of additive per weight of dry substance of the varnish.

In order to carry out the enamelling of the metal electric conductors by means of such varnishes, any usual technique can be used.

The following examples are given for mere illustrative purpose and must not to be considered as limitative of the scope of the invention.

Examples 1 to 11 illustrate the manufacture of 2,4-quinazolinedione dicarboxylic compounds.

Examples 12 to 20 illustrate the manufacture of polyester-2,4-quinazolinedione resins and their use for coating metal wires. In these examples the qualities of the enamelled wires may be estimated according to the following methods:

the flexibility of the wires is determined by subjecting them to a previous lengthening and then by winding them around their own diameter (Mandrel test 1 X). The flexibility of the enamelling material expressed in % is the maximum lengthening to which the enamelled wire may be subjected before succeeding in the winding test (i.e. without breaking of the enamelling layer).

The thermal resistance of the enamel is determined at 250°C according to the standard A.I.E.E. No. 57. It is expressed in hours.

EXAMPLE 1

41.8 g of 2-amino methyl terephthalate are dissolved in 150 ml of dioxane under an inert atmosphere, into a flask equipped with an ascenting cooler and a mechanical stirred. To this solution, there are added 25 g of 4,4'-diisocyanato-diphenylmethane and 66 mg of triethylamine acting as catalyst. The whole is brought to reflux, while maintaining the inert atmosphere and under stirring; a precipitate is formed during the first hours of heating which is continued for 47 hours.

After cooling, the precipitate is separated by filtration, thoroughly washed with ethyl ether and dried under vacuum at 100°C up to a constant weight. There is obtained 48 g of a white product having a melting point higher than 330°C, which has been identified by elementary analysis and infrared spectrum as being the 4,4'-methylene biphenylene-bis [(7-methoxycarbonyl 2,4-quinazolinedione) 3-yl]. Yield : 79.4%.

EXAMPLE 2

23.61 g of 4,4'-diisocyanato-diphenylmethane, 39.30 g of 2-amino methyl terephthalate and 100 mg of triethylenediamine, are intimately admixed, in the absence of air, in a flask provided with a small distillation column.

The mixture is heated for 30 minutes to 200°C and maintained at this temperature for 3 hours; during this time, there are recovered 5.1 g of methanol which distills from the flask. The residue is then crushed, washed with benzene, with ethanol and finally with ether.

By drying at constant weight, there are obtained 53.1 g (yield 93.3%) of a product whose infra-red spectrum is identical to that of example 1.

EXAMPLE 3

There is prepared, under dry nitrogen atmosphere, a solution of 17.3 g of methyl-amino terephthalate, 10g of 4,4'-diisocyanate-diphenylmethane and 250 mg of triethylenediamine in 60 ml of m-cresol. The solution is brought to the cresol reflux for 24 hours, and, after cooling, the formed precipitate is separated by filtration, washed with ethyl ether and brought to a constant weight by drying under vacuum at 100°C. There are thus obtained 14.8 g (yield of 61%) of a product having a melting point higher than 330°C, which is identified by elementary analysis as being 4,4'-methylene-biphenylene-bis- [(7-methoxycarbonyl-2,4-quinazolinedione)-3-yl].

EXAMPLE 4

In the same manner as described in example 2. there are reacted 12.54 g of 2-amino methyl terephthalate and 13.14 g of bis-4,4'[ N (carbophenxoy)amino ]diphenyl-methane (4,4'-diisocyanato-diphenylmethane blocked with phenol). The heating period under inert atmosphere is 47 hours, at a temperature of 200°C.

After washing and drying, there are obtained 18g (yield of 98%) of 4,4'-methylene biphenylene bis [ (7-methoxy carbonyl 2,4-quinazolinedione) 3-yl ], as indicated by the infra-red spectrum and the elementary analysis of the product.

EXAMPLE 5

A mixture of 41.8 g of 2-amino methylterephthalate having a melting point of 75.5°C, 25.2 g of 4,4'-diisocyanato diphenyl ether, 500 ml of dioxane and 5 ml of triethylamine are heated to the dioxane reflux, while stirring during 24 hours, in the absence of moisture. A rapid formation of a precipitate occurs after 1 or 2 hours of heating. After cooling and filtration, the obtained white fine precipitate is thoroughly washed with ethyl ether and then dried by heating under vacuum at 80°C.

There are thus obtained 42.1 g (yield of 70%) of a product which was identified by elementary analysis and I.R. absorption spectrum as being the 4,4'-oxybiphenylene-bis [ (7-methoxycarbonyl-2,4-quinazolinedione)-3-yl ], which has a melting point higher than 330°C.

EXAMPLE 6

7.56 g of 4,4'-diisocyanato-diphenylether and 13.0 g of 2-amino methyl terephthalate are heated at 200°-210°C under dry nitrogen atmosphere. After heating for 30 hours, the mixture is allowed to come back to room temperature and the residual product is crushed, washed with ethyl ether and dried. There are obtained 17.5 g (yield of 94%) of a product having the same structure as that obtained according to example 5.

EXAMPLE 7

41.8 g of 2-amino methylterephthalate and 35.6g of 1,6-bis-[N-( carbophenoxy)amino]-hexane are placed in a flask scavenged with an inert gas. The intimate mixture of these products, finely crushed, is then brought to 150°C for 7 hours, and thereafter to 200°C for 15 hours. After cooling, washing with ethyl ether and drying, there are recovered 38.4 g (yield of 73.5%) of 1,6-hexamethylene-bis [(7-methoxycarbonyl 2,4-quinazolinedione) 3-yl ], having a melting point of 290°C.

EXAMPLE 8

An intimate mixture of 17.4 g of 2,4-diisocyanato-toluene, 44g of 2-amino-methyl terephthalate and 0.5 g of triethylene diamine are heated progressively to 150°C under inert atmosphere. The mixture is maintained for 4 hours at 150°C, then brought to 200°C and maintained for 15 hours at this temperature. The mixture is ten cooled, the residue if finely crushed thoroughly washed with benzene, with ethanol and with ethyl ether, and then dried at constant weight under vacuum. There are thus obtained 45.77 g of 2,4-toluene bis [ (7-methoxycarbonyl 2,4-quinazolinedione) 3-yl ].

EXAMPLE 9

A solution of 19.1 g of 4-isocyanato-ethyl benzoate, 23.7 g of 2-amino ethyl terephthalate and 0.5 g of triethylamine in 150 ml of dioxane, are brought to reflux while stirring under inert atmosphere. After 20 hours of reflux, the mixture is cooled, the precipitate is separated by filtration, washed with ethyl ether and dried. There are thus obtained 47.7 g (yield of 80%) of 3-(p-ethoxycarbonyl phenyl) 7-ethoxycarbonyl 2,4-quinazolinedione.

EXAMPLE 10

18.1 g of 2-amino terephthalic acid are dissolved in a solution prepared from 8 g of sodium hydroxide and 100 ml of water. This solution is placed in a vessel provided with a very efficient stirring system adapted to carry out interfacial reactions.

To the aqueous solution, vigorously stirred, is added asolution of 25 g of 4,4'-diisocyanato-diphenylmethane in 100 ml of benzene. At the end of this addition, the stirring is continued for 2 hours at room temperature; the formed precipitate is filtrated, treated in suspension by normal hydrochloric acid, then thoroughly washed with water. After drying, there are obtained 41 g (yield of 93%) of the expected tetraacid urea.

EXAMPLE 11

20 g of the product prepared according to example 10 are heated for 5 hours at 100°C in 100 ml of a mixture by equal volumes of acetic anhydride and pyridine. After cooling, there are separated 16 g (yield of 86%) of 4,4'-methylene biphenylene bis-[ (7-carboxy 2,4-quinazolinedione) 3-yl ]having a melting point higher than 330°C.

EXAMPLE 12

In a four neck glass reaction vessel, of a 10 liters capacity, equipped with a mechanical stirrer, driven with a power engine, provided with a thermometer and a steam discharge tube, there are introduced 514.6 g of 4,4'-methylene biphenylene-bis [ (7-methoxycarbonyl-2,4-quinazolinedione) 3-yl ], 743.8 g of methyl terephthalate, 778.4 g of T.H.E.I.C. and 158.5 g of ethylene glycol, 292 g of m-cresol and 8.7 g of isopropyl titanate. The stirred mixture is brought to 200°C in 40 minutes, then maintained for 9 hours at this temperature, while continuing the stirring. During this period, 91 g of distillate are recovered by condensation of the vapors evolved from the reaction medium. the temperature is allowed to decrease down to 170°C, and the solution is diluted by adding thereto 2,333 g of m-cresol, while vigorously stirring for homogeneizing the mixture. The temperature is then allowed to decrease to 120°C and the solution is diluted by addition of 1313 g of "Solvesso 100", and 87 g of "Desmodur CTS" together with 43.5 g of isopropyl titanate are added thereto. The mixture is stirred for 2 hours at 120°C and allowed to cool down to room temperature. there is thus obtained a homogeneous solution of deep brown colour, having a viscosity at 30°C of 610 cst.

This solution is used for enamelling a copper wire of 80/100 mm, fed at a feeding rate of 1 m/minute, to a vertical oven of a 1 meter length, at a maximum temperature of 400°C. After 6 coatings, the wire is covered with an enamel layer of about 10/100 mm. This wire exhibits a homogeneous and smooth aspect.

Its flexibility is 20%, its average life time, at 250°C, is 1,200 hours, which is a far higher performance than that of the products of class H (average life time, at this temperature, of 240 hours). The enamelled wire further shows an excellent directional abrasion, a good thermoplasticity (greater than 400°C), and no loss when extracted with alcohol and toluene.

EXAMPLE 13

In a three-neck flask, equipped with a stirrer, a thermometer and a release tube, there are placed 34.25 g of 4,4'-methylene biphenylene-bis [(7-methoxycarbonyl 2,4-quinazolinedione) 3-yl ], 104.8 g of methyl terephthalate, 20 g of ethylene glycol, 100.2 g of T.H.E.I.C., 32 g of m-cresol and 500 mg of butyl-titanate. This mixture is heated to 200°C, while stirring, for 8 hours, then to 220°C for 1 hours and it is thereafter allowed to cool down. It is diluted by addition of 334 g of m-cresol and 91 g of "Solvesso 100", these additions being made at a temperature of 120°C. 2.5 g of butyl titanate and 14 g of "Desmodur CTS" are then added to the homogenized solution, and the mixture is maintained for 3 hours at 120°C. After cooling, there is obtained a homogeneous varnish, whose viscosity at 30°C is 950 cst.

This varnish has been used for enamelling a copper wire of 80/100 mm. The enamelled wire has a flexibility of 25% and its life time, measured at 250°C, is 420 hours.

EXAMPLE 14

In the same operating conditions as in example 13, there is heated a mixture consisting of:

43 g of the product obtained by condensation of 2 moles of methyl-amino terephthalate with 3 mole of 4,4'-diisocyana-to-diphenyl methane, this condensation conducted at reflux of the m-cresol for 6 hours.

46.6 g of methyl-terephthalate
52.2 g of T.H.E.I.C.
10.4 g of ethylene glycol
21.1 g of m-cresol
0.3 g of isopropyl titanate.

After heating for 10 hours at 200°c, the mixture is diluted with 164 g of m-cresol and 92 g of "Solvesso 100"; 6 g of "Desmodur CTS" are then added at a temperature of 120°C, and the mixture is stirred for 2 hours 30 minutes at this temperatue.

The resulting varnish solution has a viscosity of 1,100 cst at 30°C. It was used for coating a copper wire. The obtained enamel has a flexibility of 15%, its life time at 250°C is longer than 1,300 hours, and its resistance to abrasion is exceptional.

EXAMPLE 15

There is heated at 210°C, for 8 hours a mixture consisting of: 31.5 g of 4,4'-oxy-biphenylene-bis [ (7-methoxycarbonyl 2,4-quinazolinedione) 3-yl]

45.4 g of methyl terephzalate
44.9 g of T.H.E.I.C.
7 g of ethylene.glycol
0.5 g of isopropyl titanate
20 g of m-cresol 160 g of cresol, 80 g of Solvesso 100, 2 g of isopropyl titanate, 10 g of Desmodur CTS and 10 g of a phenol-formaldehyde resin, are added to this solution, and the resulting mixture is maintained for 2 hours at 130°C. The resulting solution has a viscosity of 880 cst at 30°C. When used for coating a cylindrical copper wire, it gives an enamelled wire exhibiting very good flexibility properties: 20 to 25% of lengthening before mandrel 1 X. Its thermal stability at 250°C is 1050 hours (higher than that of class H).

EXAMPLE 16

In a flask having three tubes, provided with a thermometer, a mechanical stirrer and a release tube for recovering the distillates, there are placed 12.5 g of 4,4'-diisocyanato-diphenylmethane, 20.9 g of methyl amino terephthalate, 0.3g of tributylamine and 24 g of m-cresol. This mixture is brought to the cresol reflux for 6 hours, under dry nitrogen atmosphere. The mixture is allowed to cool down to 150°C, and 38.8 of methyl terephthalate, 40 g of T.H.E.I.C. and 4.4g of ethyleneglycol are added thereto. As catalyst, 0.2 g of butyl titanate are also added and the whole mixture is then heated, under vigorous stirring, to 210°C, said temperature being maintained for 9 hours. The dilution of the varnish is conducted at 120°C, by successively adding 125 g of m-cresol and 75 g of Solvesso 100, so as to obtain a solution containing about 30% of dry stustance. 1 g of butyl titanate, 3 g of Desmodur CTS and 1 g of biphenyl are added to the resulting solution. After these additions, the mixture is maintained for 3 hours at 120°C under stirring. After cooling, the obtained homogeneous brown solution shows a viscosity, measured at 30°C, of 1250 cst.

A metal wire, enamelled by means of this solution, shows a deep brown coating of uniform colour and smooth aspect. It may be lengthened by 15 to 20% before being subjected with success to the test of winding around its own diameter. Its directional abrasion and its adherence index are very good. Its life time at 250°C is longer than 1000 hours.

EXAMPLE 17

In the same manner as in example 16, 41.8 g of methyl amino-terephthalate are condensed with 25.2 g of 4,4'-diisocyanato-diphenylether, in 57 g of cresol and in the presence of 0.6 g of tributylamine. After 4 hours of heating to reflux, 97 g of methyl terephthalate, 102.3 g of T.H.E.I.C., 26.8 g of ethyleneglycol and 0.7 g of isopropyl titamate are added thereto. The heating is continued at reflux for 10 hours and the mixture is then allowed to cool down to 125°C; it is then diluted by adding 250 g of cresol and 150 g of Solveso 100; there are also added 1 g of isopropyl titanate, 12g of Desmodur CTS, 15 g of phenol-formaldehyde resin and 1g of cadmium naphthenate. After maintenance for 2 hours at 120°C, the mixture shows a homogeneous aspect. At 30°C, its viscosity is 1485 cst. It gives a flexible enamelled wire (lengthening: 20%), resistant to abrasion and to heat (life time at 250°C longer than 1000 hours).

EXAMPLE 18

30.2 g of 4,4'-methylene biphenylene-bis [(7-methoxycarbonyl 2,4,-quinazolinedione) 3-yl], 49.8 g of terephthalic acid, 57.9 g of T.H.E.I.C. and 16.3 g of neopentyl-glycol, are condensed together by heating for 9 hours at 210°–220°C, in the presence of 0.6 g of isopropyl titanate and 30 g of cresylic acid.

During the heating, 3g of methanol and 9.8 g of water are recovered and removed from the reaction medium in the form of vapors, After dilution of the obtained mixture by addition of 150 g of cresylic acid and 100 g of Solvesso 100, 2.5 g of isopropyl titanate, 12.5 g of Desmodur CTS and 10 g of phenol-formaldehyde resin, are added thereto.

After heating for 3 hours at 125°C, the obtained varnish solution has a viscosity of 1310 cst at 30°C. It can be used for obtaining enamelled wires having very good mechanical properties (flexible and resistant to abrasion) as well as good thermal properties (life time at 250°C longer than 1000 hours).

EXAMPLE 19

76.4 g of 2,4-tolylene bis [(7-methoxycarbonyl 2,4-quinazolinedione) 3-yl], 155.2 g of methyl terephthalate, 37.2 g of ethylene glycol and 156.6 g of T.H.E.I.C. are admixed with 80 g of cresol and 1.5 g of isopropyl titanate. The whole mixture is brought to 210°C for 8 hours in the manner described in example 13.

The varnish is diluted by addition of 250 g of Solvesso 100 and 420 g of cresol. 3.3 g of isopropyl titanate, 15 g of Desmodur CTS, 1 g of manganese naphthenate and 15 g of phenol-formaldehyde resin are incorporated to the solution. After heating of this new mixture for 2 hours at 130°C, there is obtained a homogeneous solution having a viscosity of 1730 cst at 30°C.

Copper wires, enamelled by means of this solution, are coated with an adherent enamelling, resistant to abrasion, exhibiting a good flexibility and a good resistance to heat.

EXAMPLE 20

13.68 of 3-(p.methoxycarbonylphenyl) 7-methosycarbonyl 2,4-quinazolinedione, 19.4 g of methyl terephthalate, 20.9g of T.H.E.I.C., 5 g of ethylene glycol and 0.1 g of butyl titanate are heated for 6 hours at 200°C, while stirring with 12 g of cresol. The resulting concentrated solution is diluted by addition of 70 g of cresol and 40 g of Solvesso 100; 1 g of isopropyl titanate, 2.5 g of Desmodur CTS, 2 g of cresolformaldehyde resin are then added thereto, and the mixture is brought to 150°C for 1 hour. The resulting homogeneous solution has a viscosity of 800 cst at 30°C. Wires which have been enamelled by means of this solution are of good quality.

In the above examples, the product referred to under the trade name Solvesso 100 consists of a mixture of hydrocarbon solvents and the product referred to under the trade name Desmodur CTS is a trimer of 2,4-tolylene diisocyanate blocked with phenol.

What we claim is:

1. A polyester resin which is the reaction product resulting from condensation of a polycarboxylic component with a polyhydroxyl component, in which said polycarboxylic component comprises, expressed as carboxylic equivalents, from 10 to 100% of at least one dicarboxylic heterocyclic compound of the formula

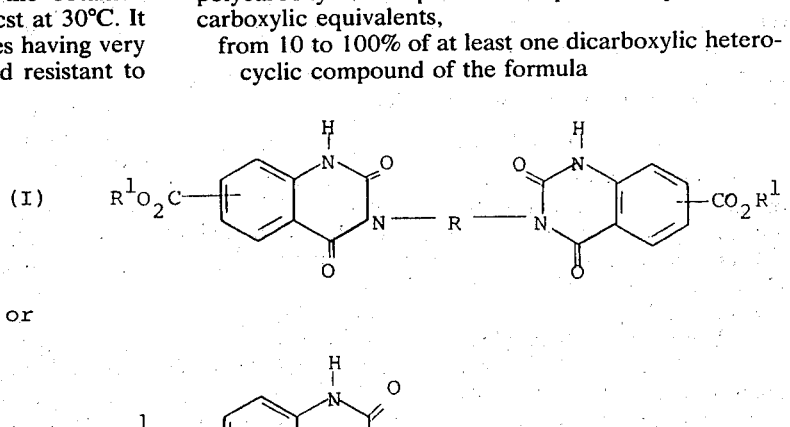

in which R is an aromatic radical of 5–20 carbon atoms, $R^1$ is a hydrogen atom or an alkyl or cycloalkyl radical of 1–10 carbon atoms and $R^2$ is an alkyl or cycloalkyl radical of 1–10 carbon atoms, from 0 to 90% of at least one polycarboxylic aromatic compound, and from 0 to 10% of at least one aliphatic dicarboxylic compound; and in which said polyhydroxyl component comprises, expressed as hydroxyl equivalents, from 50 to 100% of at least one polyol containing at least three hydroxyl functions, and from 0 to 50% of at least one aliphatic or cycloaliphatic diol; said polycarboxylic component and polyhydroxyl component being involved in such proportions that the ratio of the sum of the hydroxyl functions to the sum of the carboxylic functions is greater than 1.

2. A resin as defined by claim 1, wherein said polycarboxylic component comprises, expressed as carboxylic equivalents, from 20 to 50% of at least one dicarboxylic compound of formula (I) or (II).

3. A resin as defined by claim 1, wherein R is phenylene, tolylene, ethylphenylene, chlorophenylene, biphenylene, naphthylene, or a divalent radical of the formula:

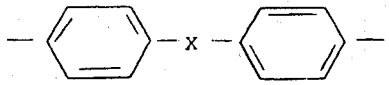

wherein X is $-O-$, $-S-$, $-SO-$, $-SO_2-$, or $-CH_2-$.

4. A resin as defined by claim 1, wherein said at least 1 dicarboxylic heterocyclic compound is of said formula (I).

5. A resin as defined by claim 1, wherein said at least 1 dicarboxylic heterocyclic compound is of said formula (II).

6. A resin as defined by claim 4, wherein R is phenylene, tolylene, or a divalent radical of diphenylmethane or diphenylether; and $R^1$ is a hydrogen atom alkyl of 1–6 carbon atoms.

7. A resin as defined by claim 5, wherein R is phenylene and $R^1$ and $R^2$ are each alkyl of 1–6 carbon atoms.

8. A resin as defined by claim 6, wherein said dicarboxylic heterocyclic compound is selected from the group consisting of 4,4'-methylene biphenylene-bis [(7-carboxy 2,4-quinazolinedione) 3-yl], the dimethyl ester thereof and the diethyl ester thereof.

9. A resin as defined by claim 6, wherein said dicarboxylic heterocyclic compound is selected from the group consisting of 4,4'-oxybiphenylene-bis [(7-carboxy 2,4-quinazolinedione) 3-yl], the dimethyl ester thereof and the diethyl ester thereof.

10. A resin as defined by claim 6, wherein said dicarboxylic heterocyclic compound is selected from the group consisting of 2,4-tolylene bis [(7-carboxy 2,4-quinazolinedione) 3-yl], the dimethyl ester thereof and the diethyl ester thereof.

11. A resin as defined by claim 7, wherein said dicarboxylic heterocyclic compound is selected from the group consisting of 3-(p.methoxycarbonyl phenyl)7-methoxylcarbonyl 2,4-quinazolinedione and 3-(p.ethoxy-carbonyl-phenyl) 7-ethoxycarbonyl 2,4-quinazolinedione.

12. A resin as defined by claim 1, wherein said at least one polycarboxylic aromatic compound is isophthalic acid, terephthalic acid, 4,4'-diphenyl-ether dicarboxylic acid, trimesic acid or trimellitic acid, of the lower alkyl esters thereof.

13. A resin as defined by claim 1, wherein said at least one dialiphatic dicarboxylic compound is maleic, adipic, azelaic or sebacic acid, of the lower alkyl esters thereof.

14. A resin as defined by claim 1, wherein said at least one polyol containing at least three hydroxyl functions is glycerol, 1,1,1-trimethylol ethane, 1,1,1-trimethylol propane, pentaerythritol, sorbitol, mannitol, tris (hydroxyethyl) isocyanurate, or tris (hydroxypropyl) isocyanurate.

15. A resin as defined by claim 1, wherein said at least one aliphatic or cycloaliphatic diol is ethyleneglycol, 1,4-butanediol, 1,5-pentanediol, neopentylglycol, 1,6-hexanediol, 1,6-trimethylhexanediol or 1,4-cyclohexanediol.

16. A resin as defined by claim 1, wherein said polycarboxylic aromatic compound is methyl terephthalate, said polyol containing at least three hydroxyl functions is tris (hydroxyethyl) iso-cyanurate and said diol is ethyleneglycol or neopentylglycol.

17. A composition comprising at least one polyester resin according to claim 1, diluted in a solvent.

18. A composition as defined by claim 17, containing 1–15% by weight of a polyisocyanate.

19. A composition as defined by claim 17, which further comprises about 0.1–1% by weight of a metal drying agent.

* * * * *

UNITED STATES PATENT AND TRADEMARK OFFICE
CERTIFICATE OF CORRECTION

PATENT NO. : 3,985,711
DATED : October 12, 1976
INVENTOR(S) : Choua Cohen et al.

It is certified that error appears in the above—identified patent and that said Letters Patent are hereby corrected as shown below:

[73] Assignee: should read --INSTITUT FRANCAIS DU PETROLE
Des Carburants & Lubrifiants --.

Signed and Sealed this

Eighth Day of March 1977

[SEAL]

Attest:

RUTH C. MASON
Attesting Officer

C. MARSHALL DANN
Commissioner of Patents and Trademarks